(12) United States Patent
Chang et al.

(10) Patent No.: US 10,493,104 B2
(45) Date of Patent: *Dec. 3, 2019

(54) COMPOSITION FOR TREATING INFLAMMATORY BRAIN DISEASES WHICH INCLUDES STEM CELL AS ACTIVE INGREDIENT

(71) Applicant: SAMSUNG LIFE PUBLIC WELFARE FOUNDATION, Seoul (KR)

(72) Inventors: Yun Sil Chang, Seoul (KR); Won Soon Park, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/768,734

(22) PCT Filed: Feb. 19, 2014

(86) PCT No.: PCT/KR2014/001332
§ 371 (c)(1),
(2) Date: Aug. 18, 2015

(87) PCT Pub. No.: WO2014/129792
PCT Pub. Date: Aug. 28, 2014

(65) Prior Publication Data
US 2016/0000831 A1 Jan. 7, 2016

(30) Foreign Application Priority Data
Feb. 20, 2013 (KR) .................. 10-2013-0017935

(51) Int. Cl.
*A61K 35/28* (2015.01)
*A61K 35/545* (2015.01)
(Continued)

(52) U.S. Cl.
CPC .............. *A61K 35/28* (2013.01); *A61K 35/12* (2013.01); *A61K 35/54* (2013.01); *A61K 35/545* (2013.01)

(58) Field of Classification Search
CPC ........ A61K 35/28; A61K 35/54; A61K 35/12; A61K 35/345
(Continued)

(56) References Cited

U.S. PATENT DOCUMENTS 8,057,788 B2 * 11/2011 Hariri ................. C12N 5/0605
424/93.1
2012/0269774 A1 10/2012 Ichim
2013/0004465 A1 * 1/2013 Aberman ............... A61K 35/50
424/93.7

FOREIGN PATENT DOCUMENTS

EP 1 845 154 A1 10/2007
KR 1020110087263 A 8/2011
(Continued)

OTHER PUBLICATIONS

Roobrouck et al. Concise Review: Culture Mediated Changes in Fate and/or Potency of Stem Cells. Stem Cells (2011), v29(4), p. 583-589.*

(Continued)

*Primary Examiner* — Sean C. Barron
(74) *Attorney, Agent, or Firm* — Harness, Dickey & Pierce, P.L.C.

(57) ABSTRACT

The present invention relates to a composition for treating inflammatory brain diseases which includes a stem cell as an active ingredient. When the stem cell according to the present invention is directly administered to animal models with inflammatory brain diseases, a brain damage caused by inflammation such as edema is significantly reduced, the weight-loss phenomenon is greatly improved, and the like, and thus the cell has an excellent effect in treating inflam- (Continued)

matory brain diseases and consequently can be used effectively in treating inflammatory brain diseases.

4 Claims, 3 Drawing Sheets

(51) Int. Cl.
A61K 35/12 (2015.01)
A61K 35/54 (2015.01)
(58) Field of Classification Search
USPC .................................................. 435/366, 325
See application file for complete search history.

(56) References Cited

FOREIGN PATENT DOCUMENTS

| KR | 1020120013923 | | 2/2012 | |
|---|---|---|---|---|
| WO | WO-2005042703 A2 | * | 5/2005 | ........... C12N 5/0605 |
| WO | 2006044204 A2 | | 4/2006 | |
| WO | 2008036374 A2 | | 3/2008 | |
| WO | WO 2008/0036734 | * | 3/2008 | |
| WO | 2009129616 A1 | | 10/2009 | |
| WO | 2010141606 A2 | | 12/2010 | |

OTHER PUBLICATIONS

Peters et al. Efficient Generation of Multipotent Mesenchymal Stem Cells from Umbilical Cord Blood in Stroma-Free Liquid Culture. PloS One (2010), v5(12), e15689, 14 pages.*
Tondreau et al. Mesenchymal Stem Cells Derived from CD133-Positive Cells in Mobilized Peripheral Blood and Cord Blood: Proliferation, Oct4 Expression, and Plasticity. Stem Cells (2005), v23, p. 1105-1112.*
Suila et al. Are globoseries glycosphingolipids SSEA-3 and -4 markers for stem cells derived from human umbilical cord blood? Journal of Molecular Cell Biology (2011), p. 99-107.*
Lee et al. Isolation of multipotent mesenchymal stem cells from umbilical cord blood. Blood (2004), v103, p. 1669-1675.*
Haase et al. Successful treatment of Bacillus cereus meningitis following allogenic stem cell transplantation. Pediatric Transplantation (2005), v9, p. 338-341.*
Thigpen et al. Bacterial Meningitis in the United States, 1998-2007. The New England Journal of Medicine (2011), v364, p. 2016-2025.*
Meningoencephalitis. (2010). In H. Marcovitch (Ed.), Black's medical dictionary, 42nd edition (42nd ed.).*
Linder et al. Mesenchymal Stem or Stromal Cells: Toward a Better Understanding of Their Biology? Transfusion Medicine and Hemotherapy (2010), v37, p. 75-83. (Year: 2010).*
Archimbaud et al. Molecular Evidence of Persistent Echovirus 13 Meningoencephalitis in a Patient with Relapsed Lymphoma after an Outbreak of Meningitis in 2000. Journal of Clinical Microbiology (2003), v41(10), p. 4605-4610. (Year: 2003).*
Sovinz et al. Severe Epstein-Barr Virus Encephalitis With Hemophagocytic Syndrome. The Pediatric Infectious Disease Journal (2010), v29(6), p. 553-556. (Year: 2010).*
Ferreira et al. Familial haemophagocytic lymphohistiocytosis: two case reports. BMJ Case Rep. (2010), 5 page reprint. (Year: 2010).*
Gyurkocza et al. Allogeneic hematopoietic cell transplantation: the state of the art. Exp. Rev Hematol. (2010), v3(3), 27 page manuscript. (Year: 2010).*
Ahn et al. Mesenchymal Stem Cells Prevent Hydrocephalus After Severe Intraventricular Hemorrhage. Stroke. 2013;44:497-504. (Year: 2013).*
International Search Report and Written Opinion for corresponding application PCT/KR2014/001332 dated Jun. 2, 2014.
European Office Action from corresponding EP Application No. 14754748.3 dated Apr. 18, 2018.
Extended European Search Report from corresponding EP Application No. 14754748.3 and PCT/KR2014001332 dated Jul. 20, 2016.
Van Velthoven, C. T. J., et al.; Mesenchymal stem cells as a treatment for neonatal ischemic brain damage, Pediatric Research, vol. 71, No. 4, Apr. 2012, pp. 474-481.
Al Jumah, M. A., et al.; The Immunomodulatory and Neuroprotective Effects of Mesenchymal Stem Cells (MSCs) in Experimental Autoimmune Encephalomyelitis (EAE): A Model of Mutliple Sclerosis (MS); Int. J. Mol. Sci. 2012, 13, 9298-9331.
Examination Report from corresponding European Patent Application No. 14754748.3, dated Dec. 18, 2018.

* cited by examiner

[Fig. 1]
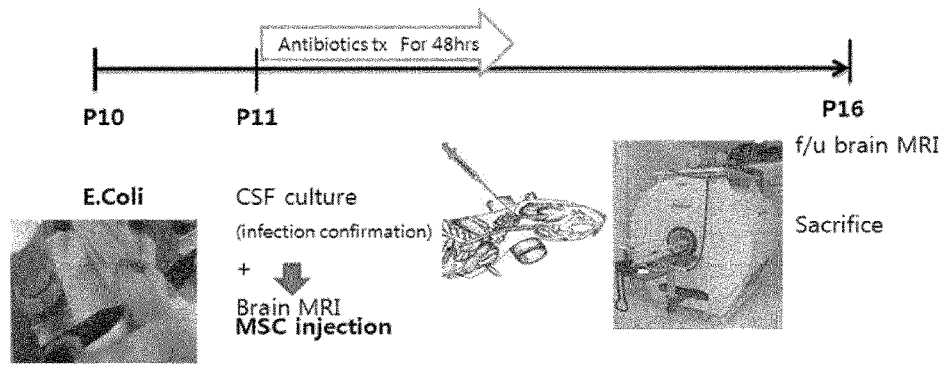
[Fig. 2]
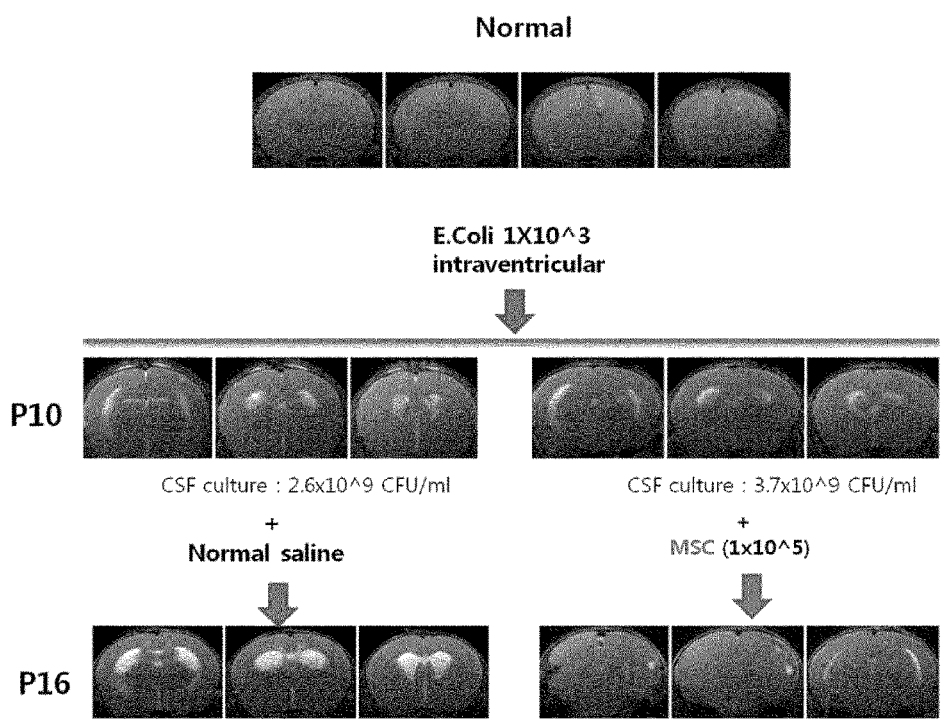
[Fig. 3]
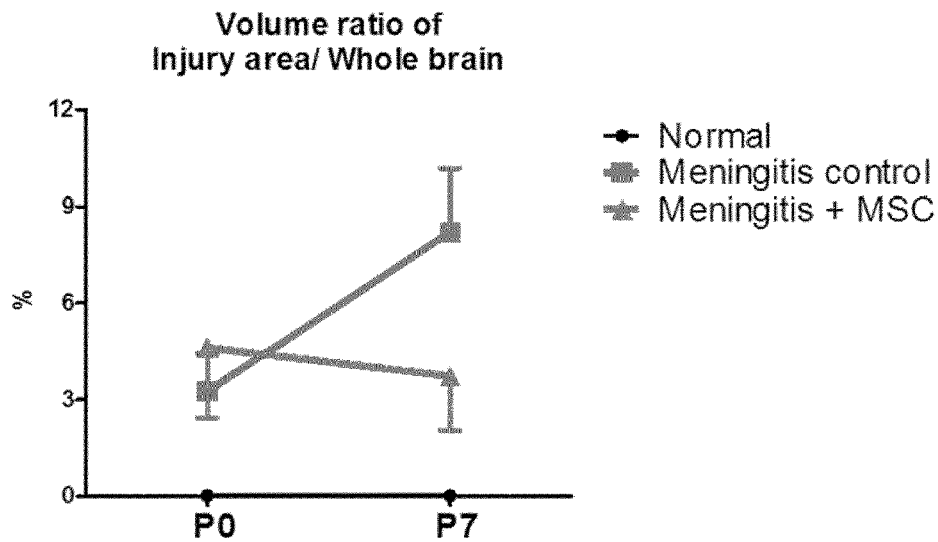

[Fig. 4]
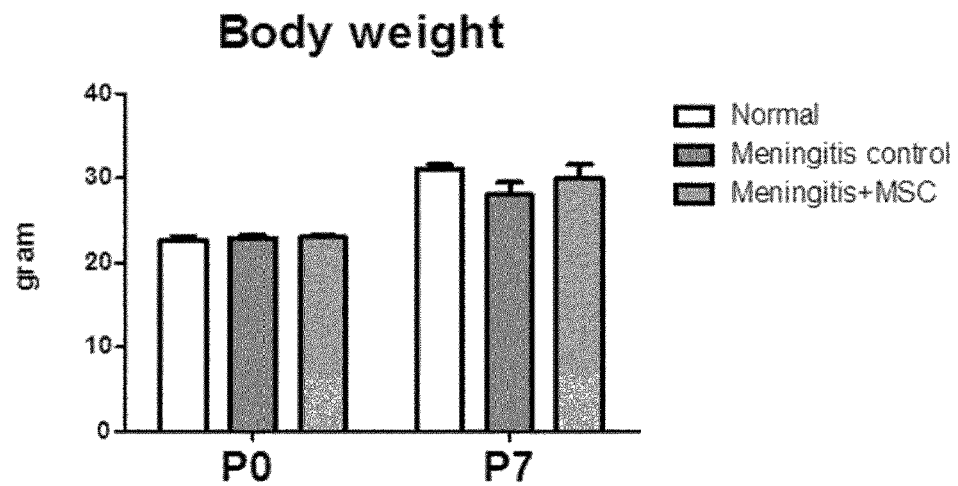
[Fig. 5]
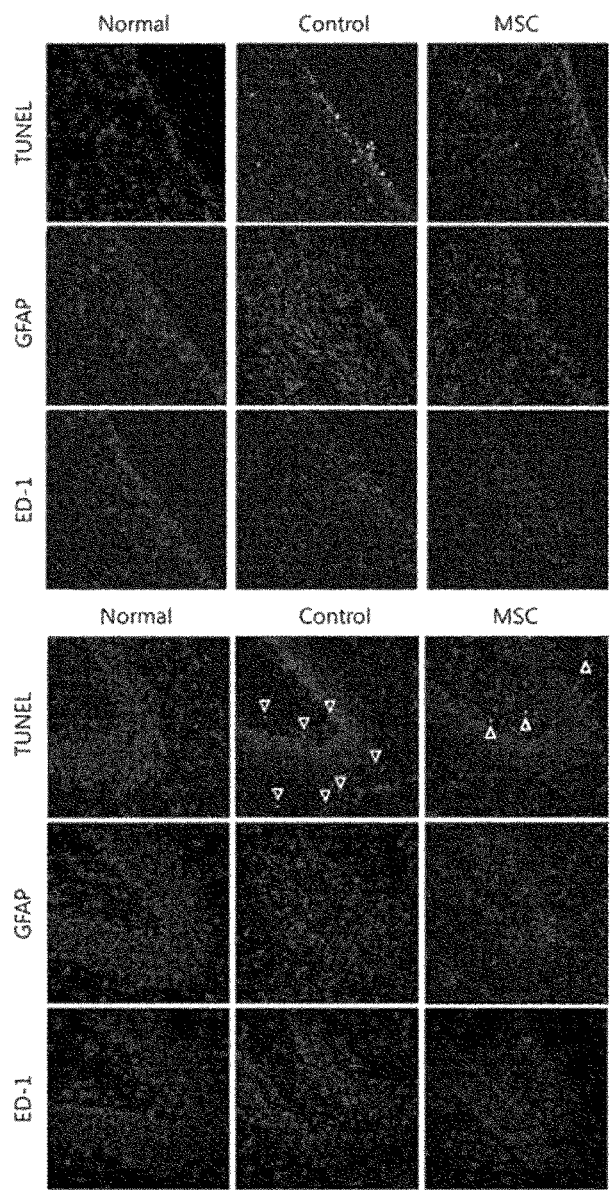

[Fig. 6]
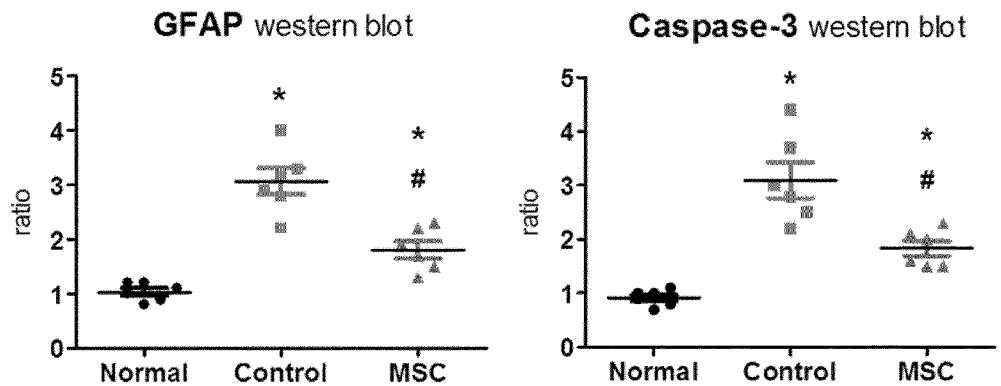
*, P<0.05 vs. Normal
, P<0.05 vs. Control
[Fig. 7]
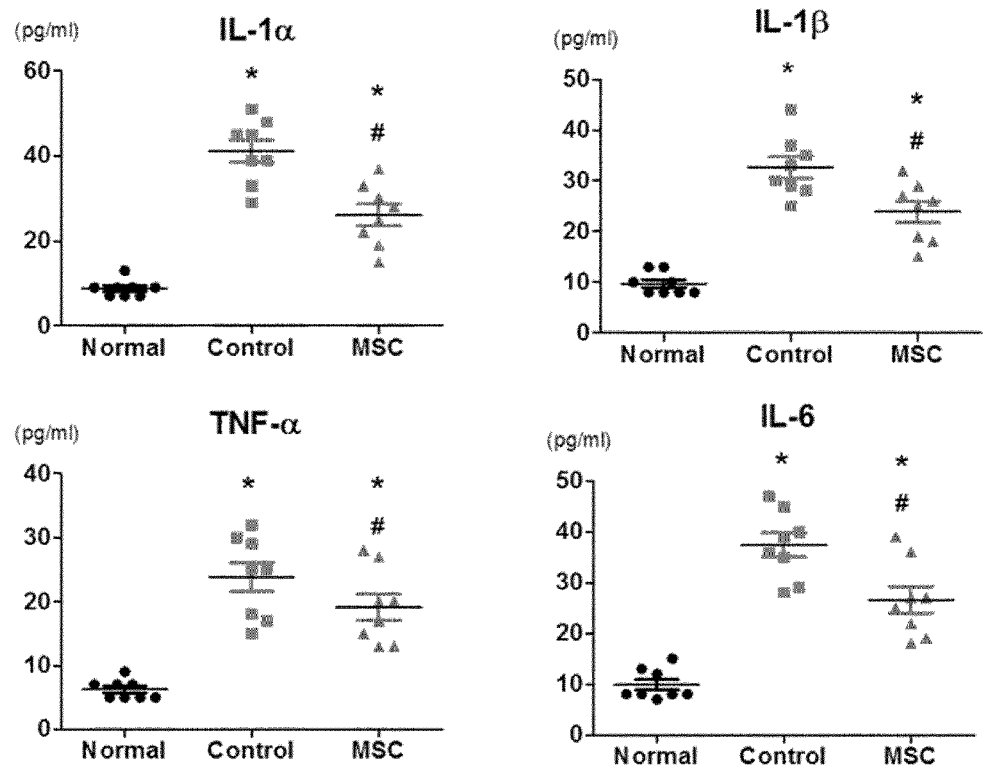
*, P<0.05 vs. Normal
, P<0.05 vs. Control // COMPOSITION FOR TREATING INFLAMMATORY BRAIN DISEASES WHICH INCLUDES STEM CELL AS ACTIVE INGREDIENT

TECHNICAL FIELD

The present invention relates to a composition for treating inflammatory brain diseases, comprising stem cells as an active ingredient.

BACKGROUND ART

Stem cells refer to cells having the ability to self-replicate and the ability to differentiate into at least two cells and can be classified into totipotent stem cells, pluripotent stem cells, and multipotent stem cells.

Totipotent stem cells are cells with totipotent properties capable of developing into one perfect individual, and these properties are possessed by cells up to the 8-cell stage after the fertilization of an ovum by a sperm. When these cells are isolated and transplanted into the uterus, they can develop into one perfect individual.

Pluripotent stem cells, which are cells capable of developing into various cells and tissues derived from ectodermal, mesodermal and endodermal layers, are derived from an inner cell mass located inside blastocysts generated 4-5 days after fertilization. These cells are called embryonic stem cells and can differentiate into various other tissue cells but not create new living organisms.

Multipotent stem cells are stem cells capable of differentiating into only cells specific to tissues and organs containing these cells and are involved in the growth and development of each tissue and organ during fetal, neonatal, and adult periods as well as the maintenance of homeostasis of adult tissues and the induction of regeneration of damaged tissues. These tissue-specific multipotent cells are collectively referred to as adult stem cells. Adult stem cells are taken from pre-existing cells in various organs of the human body and then developed into stem cells, and these cells are characterized by differentiation into specific tissues. However, experiments for differentiating adult stem cells into various tissues such as hepatocytes have been performed successfully and thus have attracted much attention.

Stem cells have properties such as self-renewal, differentiation, and immortality, and adult stem cells, which can be obtained from various tissues, can be derived from various sources, compared to embryonic stem cells. Moreover, adult stem cells can avoid ethical issues that researchers can encounter and thus have been widely used in studies. Furthermore, stem cells isolated from umbilical cord blood do not cause any additional damage to a donor, unlike bone marrow or adipose tissue, and thus have more advantages than other adult stem cells.

Meanwhile, inflammatory brain diseases refer to inflammatory diseases occurring in the brain due to specific causes and encompass encephalitis, meningitis, meningoencephalitis, etc. Encephalitis is the generic term for inflammatory diseases of the cerebral parenchyma and is distinguished from inflammation of the meninges surrounding the brain (meningitis). When meningitis and encephalitis are both present, this is frequently referred to as meningoencephalitis. Depending on the causes, encephalitis can be broadly divided into infectious, vasculitic, tumoral, chemical, and idiopathic encephalitis and can be divided again into specific categories depending on the details.

Moreover, the encephalitis can be divided into acute, subacute, and chronic encephalitis depending on the time course of the disease. Until now, antibiotics have been used for the treatment of inflammatory brain diseases, but even if the causative organisms are treated by the use of antibiotics, they cause side effects such as acute brain injury, hydrocephalus, hypacusis, epilepsy, etc., and thus there is a need to develop a new treatment for inflammatory brain diseases. However, there have been no systematic studies on the treatment of inflammatory brain diseases using stem cells so far.

Accordingly, the present inventors have conducted research to develop a new medicine for treating inflammatory brain diseases and found that direct administration of stem cells into the ventricles of animal models with inflammatory brain diseases has excellent therapeutic effects on inflammatory brain diseases, such as causing less side effects such as significantly reduced brain injury due to inflammatory response such as edema and significantly reduced loss in weight, reducing the degree of apoptosis and reactive gliosis, and significantly reducing the number of activated macrophages and the number of inflammatory cytokines in the brain, thereby completing the present invention.

DISCLOSURE

Technical Problem

An object of the present invention is to provide a pharmaceutical composition for treating inflammatory brain diseases, comprising stem cells as an active ingredient.

Technical Solution

To accomplish the above object, the present invention provides a pharmaceutical composition for treating inflammatory brain diseases, comprising stem cells as an active ingredient.

Advantageous Effects

When the stem cells according to the present invention are administered directly into the ventricles of animal models with inflammatory brain diseases, they have excellent therapeutic effects on inflammatory brain diseases, such as causing less side effects such as significantly reduced brain injury due to inflammatory response such as edema and significantly reduced loss in weight, reducing the degree of apoptosis and reactive gliosis, and significantly reducing the number of activated macrophages and the number of inflammatory cytokines in the brain, and thus can be effectively used for the treatment of inflammatory brain diseases.

DESCRIPTION OF DRAWINGS

FIG. 1 shows the experimental design to determine the therapeutic effect of stem cells on inflammatory brain diseases.

FIG. 2 shows MRI images of brains that have been changed depending on the induction of brain inflammation and the administration of stem cells.

FIG. 3 shows the changes in the ratio of the brain injury area to the total brain area depending on the administration of stem cells in meningoencephalitis animal models.

FIG. 4 shows the changes in body weight depending on the administration of stem cells in meningoencephalitis animal models.

FIG. 5 shows the results of immunofluorescence stainings of brain tissues depending on the administration of stem cells in meningoencephalitis animal models.

FIG. 6 shows the changes in protein expression in brain tissues depending on the administration of stem cells in meningoencephalitis animal models.

FIG. 7 shows the changes in inflammatory cytokine expression in brain tissues depending on the administration of stem cells in meningoencephalitis animal models.

MODE FOR INVENTION

The present invention provides a pharmaceutical composition for treating inflammatory brain diseases, comprising stem cells as an active ingredient.

In the present invention, the stem cells refer to cells that are the source of cells or tissues that constitute an individual and may refer to undifferentiated cells that have the ability to differentiate into specific cells or multiple functional cells and the ability to self-replicate the same cells repeatedly. Stem cells are present in all tissues during fetal development and can be found in some adult tissues such as bone marrow, epithelial tissues, etc. where cells are continually replaced.

The stem cells may be autologous or allogeneic stem cells, may be derived from any kind of animals including human and non-human mammals, and may include both adult- and embryonic-derived stem cells without limitation.

Moreover, the stem cells of the present invention include embryonic stem cells or adult stem cells and are preferably adult stem cells. The adult stem cells may be mesenchymal stem cells, human tissue-derived mesenchymal stromal cells, human tissue-derived mesenchymal stem cells, multipotent stem cells, or amniotic epithelial cells, and the mesenchymal stem cells may be derived from at least one selected from the group consisting of umbilical cord, umbilical cord blood, bone marrow, adipose, muscle, nerve, skin, amnion, and placenta, but not limited thereto. In an embodiment of the present invention, umbilical cord blood-derived mesenchymal stem cells were used as the stem cells.

More specifically, the stem cells used in an embodiment of the present invention were isolated from umbilical cord blood and cultured, and the stem cells express CD105 and CD73 markers but do not express CD34, CD45 and CD14 markers. Moreover, the stem cells are positive for HLA-AB and negative for HLA-DR and express pluripotent markers such as Oct4 and SSEA-4.

In order to obtain the stem cells of the present invention, the way to isolate and collect umbilical cord blood is as follows. During normal vaginal delivery, umbilical cord blood is collected from the umbilical vein extracted from the uterus in which the placenta remains after childbirth, and during cesarean section, umbilical cord blood is collected from the umbilical vein while the placenta is expelled from the uterus after childbirth. When umbilical cord blood is collected from the umbilical vein extracted from the uterus after childbirth, it is collected from the umbilical vein connecting the placenta and fetus after an infant is born by aseptic technique. At this time, a method of collecting umbilical cord blood before the separation of the placenta from the uterus after childbirth or a method of collecting umbilical cord blood in vitro after the separation of the placenta can be used. During cesarean section, the method of collecting umbilical cord blood in vitro after the separation of the placenta is used, in which the umbilical cord blood is collected in a blood bag containing an anticoagulant using a collecting needle after securing the umbilical vein.

Methods of isolating and culturing mesenchymal stem cells from collected umbilical cord blood include a method disclosed in Korean Patent Publication No.: 2003-0069115 and methods known in the art (Pittinger M F et al. Science, 284: 143-7, 1999; and Lazarus H M et al. Bone Marrow Transplant, 16: 557-64, 1995), and an example is as follows. First, the collected umbilical cord blood is centrifuged on a Ficoll-Hypaque gradient, for example, to isolate mononuclear cells including hematopoietic stem cells and mesenchymal stem cells, which are then washed several times to remove impurities. When the washed mononuclear cells are seeded in a culture vessel at an appropriate density and cultured, the cells proliferate as a monolayer. Among these cells, those that are homogeneous with an elongated spindle shape and proliferate in the form of a colony, when observed by phase contrast microscopy, are mesenchymal stem cells. Then, when these cells are cultured and grown, the cells are allowed to proliferate by subculture up to a desired number of cells.

In the present invention, a cell culture medium containing 10% to 30% FBS can be used for the isolation and culture of mesenchymal stem cells, and the cell culture medium may include those typically used in the art, such as Dulbecco's modified eagle medium (DMEM), minimal essential medium (MEM), alpha-MEM, McCoy's 5A medium, Eagle's basal medium, Connaught Medical Research Laboratory (CMRL) medium, Glasgow MEM, Ham's F-12 medium, Iscove's modified Dulbecco's medium (IMDM), Leibovitz' L-15 medium, Roswell Park Memorial Institute (RPMI) 1640 medium, etc.

When the stem cells according to the present invention are administered directly into the ventricles of animal models with inflammatory brain diseases, they have excellent therapeutic effects on inflammatory brain diseases, such as causing less side effects such as significantly reduced brain injury due to inflammatory response such as edema and significantly reduced loss in weight, reducing the degree of apoptosis and reactive gliosis, and significantly reducing the number of activated macrophages and the number of inflammatory cytokines in the brain, and thus can be effectively used for the treatment of inflammatory brain diseases.

In the present invention, the inflammatory brain diseases collectively refer to all inflammatory diseases occurring in the brain and include encephalitis, meningitis, and meningoencephalitis, but not limited thereto.

The pharmaceutical composition of the present invention may further comprise one or more known active ingredient having the therapeutic effect on inflammatory brain diseases in combination with the stem cells.

The pharmaceutical composition of the present invention may be formulated into a dosage form suitable for administration to an individual according to conventional methods in the pharmaceutical field. Examples of dosage forms suitable for this purpose may preferably include those for parenteral administration such as injections including injection ampoules, infusions including infusion bags, and spraying agents including aerosols. The injection ampoules may be mixed with injection solutions immediately before use, and the injection solutions may include physiological saline, glucose, Ringer's solution, etc. Moreover, the infusion bags may be made of polyvinyl chloride or polyethylene.

The pharmaceutical composition of the present invention may further comprise a suitable carrier conventionally used for the preparation of pharmaceutical compositions. For example, in the case of injections, they may further comprise a preservative, an analgesic agent, a solubilizing agent, or a stabilizing agent, and in the case of dosage forms for topical administration, they may further comprise a base, an excipient, a lubricant, or a preservative.

As used herein, the term "administration" refers to providing the composition of the present invention to an individual in an arbitrary suitable way. For a desired effect, the stem cells may be administered in a daily dose of $1.0 \times 10^2$ to $1.0 \times 10^{10}$ cells/kg body weight once or several times. However, it should be understood that the dose of the active ingredient actually administered ought to be determined in light of various relevant factors such as the condition to be treated, the route of administration, the age, the body weight, age, and sex of an individual, and the above dose should not be intended to limit the scope of the invention in any way.

The pharmaceutical composition of the present invention may be administered into an individual via various routes. All routes of administration can be contemplated and include, for example, oral or rectal administration, or intravenous, intramuscular, subcutaneous, intrauterine, or intracerebrovascular injection. Preferably, the pharmaceutical composition of the present invention can be grafted or transplanted directly to the ventricle of an individual in need of treatment, but not limited thereto.

The composition of the present invention can be used alone or in conjunction with surgery, radiation therapy, hormone therapy, chemical therapy, and methods using biological response modifiers for the treatment of inflammatory brain diseases.

Hereinafter, preferred examples will be provided for better understanding of the present invention. However, the following examples are only provided to illustrate the present invention, and the scope of the present invention is not limited by the examples.

Example 1: Preparation and Characterization of Mesenchymal Stem Cells

The following experiment was performed to isolate mesenchymal stem cells from human umbilical cord blood. First, collected umbilical cord blood was centrifuged on a Ficoll-Hypaque gradient to isolate mononuclear cells including hematopoietic stem cells and mesenchymal stem cells, which were then washed several times to remove impurities. After washing, the mononuclear cells were seeded in a culture vessel and cultured, and among the cells that proliferated as a monolayer, mesenchymal stem cells which were homogeneous with an elongated spindle shape and proliferated in the form of a colony, when observed by phase contrast microscopy, were isolated and proliferated by subculture. Umbilical cord blood-derived mesenchymal stem cells subcultured for 5 passages were characterized.

As a result, it was found that the stem cells of the present invention expressed CD105 and CD73 markers, but did not express CD34, CD45 and CD14 markers. Moreover, it was found that the stem cells were positive for HLA-AB and negative for HLA-DR and expressed pluripotent markers such as Oct4 and SSEA-4.

Example 2: Transplantation of Mesenchymal Stem Cells into Ventricles of Meningoencephalitis Animal Models and Determination of Effects on Treatment of Meningoencephalitis 2-1. Design of Meningoencephalitis Animal Models To create meningoencephalitis animal models, after 10-day-old white rats were anesthetized by inhalation of nitrogen monoxide, *Escherichia coli* (*E. coli*) of $1 \times 10^3$ colony forming unit (CFU) (10 ul) was slowly administered into the right ventricle using a 31 gauge syringe for 60 seconds on a stereotaxic frame, and then an antibiotic Ampicillin (200 mg/kg) was administered every 12 hours for 2 days. To identify the effects of the stem cells of the present invention on the treatment of meningoencephalitis, $1 \times 10^5$ mesenchymal stem cells were diluted in 10 ul PBS and slowly administered into the right ventricle of white rats at the age of 11 days (P11), one day after the modeling (induction of meningoencephalitis), on a stereotaxic frame under inhalation anesthesia of nitrogen monoxide. In the meningoencephalitis control, physiological saline was administered into the right ventricle. The above experiment process is shown in FIG. 1.

2-2. Brain MRI Scans and Body Weights Measurement

MRI scans of brain, culture of cerebrospinal fluid, and measurement of body weight were performed on the meningoencephalitis animal models established in the above Example 2-1. More specifically, one day after the induction of meningoencephalitis, the brains of 11-day-old white rats (P11) were scanned by 7-tesla magnetic resonance imaging (MRI), and the degree of injury due to meningoencephalitis was measured on the diffusion weighted image (DWI). Furthermore, in order to identify the cerebrospinal fluid infection, each white rat underwent a cistern tap to obtain cerebrospinal fluid, which was cultured to identify *E. coli*. Then, the brains of all white rats at the age of 16 days (P16) were scanned by 7-tesla MRI to measure the degree of brain injury. Brain MRI images were analyzed with an Image J program to measure the increase in ventricle and the infarcted area of cerebral parenchyma, which was defined as brain injury, and "the volume ratio of the brain injury area to the total brain area" was calculated. Moreover, the body weight of each white rat was measured before and after the experiment.

The experimental results are shown in FIGS. 2 to 4.

As shown in FIG. 2, compared to the 11-day-old white rats (Normal), the meningoencephalitis-induced white rats (P11) showed severe edema and injury in cerebral parenchyma and ventricular dilatation, and it was found that the meningoencephalitis was induced by the growth of *E. coli* during the cerebrospinal fluid culture test. Moreover, it was found from the brain MRIs taken at the age of 16 days (P16) that when the stem cells were administered into the ventricle of white rats after the induction of meningoencephalitis, the degree of ventricular dilatation was significantly reduced compared to the white rats which were not treated with stem cells.

Moreover, as shown in FIG. 3, the brain injury was increased in the meningitis group compared to the normal white rats (Normal), and before the administration of the substances (P0), there were no differences in the degree of brain injury between the meningitis control into which physiological saline was administered and the meningitis group treated with the stem cell of the present invention (Meningitis+MSC). However, after the administration of the substances (P7), the brain injury was significantly increased in the meningitis control, while the brain injury was not increased in the meningitis group treated with the stem cell of the present invention, from which it was found that the degree of brain injury was significantly improved by the administration of the stem cells of the present invention after the induction of meningoencephalitis.

Furthermore, as shown in FIG. 4, the average body weights between all groups were similar at the start point of the experiment (P0). However, it was found that after the administration of the substances (P7), the body weights were significantly reduced due to weakened body conditions caused by meningitis in the meningitis control (Meningitis control) in which meningitis was induced and which were not treated with stem cells, but the reduction in body weight was significantly low in the meningitis group treated with the stem cell of the present invention (Meningitis+MSC).

2-3. Staining of Brain Tissues and Analysis of Protein Expression

After the end of the experiment on the meningoencephalitis animal models established in the above Example 2-1 (at the age of 16 days (P16)), each white rat was anesthetized by intraperitoneal injection of ketamine. Then, cerebrospinal fluid (CSF) was collected from the cistern magna of each white rat, which was then quickly frozen and stored at −70° C.

Moreover, after fixing the extremities of each white rat, the chest was incised to expose heart and lung tissues, a 23 gauge needle was inserted into the left ventricle, and then 4% paraformaldehyde was perfused into the right atrium. Then, the skull was incised, and brain tissues were carefully collected and fixed in 4% formalin, or periventricular areas were cut, which were then quickly frozen in nitrogen gas and stored at −70° C.

Immunofluorescence stainings such as immunofluorescent terminal deoxynucleotidyl transferase-mediated deoxyuridine triphosphate nick end labeling (TUNEL), neuronal specific glial fibrillary acidic protein (GFAP), and ED-1 were performed according to a known method on the brain tissues isolated by the above process, and the expression of GFAP and Caspase-3 was identified by Western blot.

Moreover, the expression of inflammatory cytokines (IL-1, IL-β, IL-6, TNF-α) was measured by the known enzyme-linked immunosorbent assay (ELISA) using the periventricular areas and cerebrospinal fluid isolated by the above process.

The experimental results are shown in FIGS. 5 to 7.

As shown in FIG. 5, the results of the TUNEL staining show that the degree of apoptosis in cells that were positive for the staining was significantly increased in the meningitis control (Control) in which meningitis was induced and which were not treated with stem cells, compared to the normal white rats (Normal), but it was significantly reduced in the group (MSC) treated with the stem cell of the present invention. Moreover, the results of the GFAP staining show that the degree of reactive gliosis in cells that were positive for the staining was significantly increased in the meningitis control (Control) in which meningitis was induced and which were not treated with stem cells, compared to the normal white rats (Normal), but it was significantly reduced in the group (MSC) treated with the stem cell of the present invention. Furthermore, the results of the ED-1 staining show that the number of activated macrophages in the brain that were positive for the staining was significantly increased in the meningitis control (Control) in which meningitis was induced and which were not treated with stem cells, compared to the normal white rats (Normal), but it was significantly reduced in the group (MSC) treated with the stem cell of the present invention.

Moreover, as shown in FIG. 6, the results of the Western blot analysis show that the ratio of GFAP to Caspase-3 was significantly increased in the meningitis control (Control) in which meningitis was induced and which were not treated with stem cells, compared to the normal white rats (Normal). However, the ratio of GFAP to Caspase-3, from which the degree of reactive gliosis and the degree of apoptosis can be determined, was significantly reduced in the group (MSC) treated with the stem cell of the present invention.

Furthermore, as shown in FIG. 7, the results of the ELISA analysis show that the expression of inflammatory cytokines in the brain was sharply increased in the meningitis control (Control) in which meningitis was induced and which were not treated with stem cells, compared to the normal white rats (Normal). However, the number of inflammatory cytokines was significantly improved in the group (MSC) treated with the stem cell of the present invention.

It was found from the above experimental results that the stem cells according to the present invention can treat inflammatory brain diseases through transplantation into the ventricles.

The invention claimed is:

1. A method for treating encephalitis or meningoencephalitis, comprising administering to a subject in need thereof an effective amount of stem cells,
   wherein the stem cells are mesenchymal stem cells,
   wherein the encephalitis or meningoencephalitis is treated by the administered stem cells,
   wherein the encephalitis or meningoencephalitis is induced by one or more infectious agents selected from the group consisting of bacteria, parasites, fungi, protozoa, and combinations thereof, and
   wherein the stem cells are administered directly to a ventricle of the subject.

2. The method according to claim 1, wherein the stem cells are autologous or allogeneic stem cells.

3. The method according to claim 1, wherein the mesenchymal stem cells are derived from at least one selected from the group consisting of umbilical cord, umbilical cord blood, bone marrow, adipose, muscle, nerve, skin, amnion, and placenta.

4. The method according to claim 1, wherein the stem cells have the following immunological characteristics:
   (1) positive for CD105, CD73, and HLA-AB;
   (2) negative for CD34, CD45, CD14, and HLA-DR; and
   (3) expression of Oct4 and SSEA-4.

* * * * *